United States Patent
Goeldner

(12) 
(10) Patent No.: US 6,495,095 B1
(45) Date of Patent: Dec. 17, 2002

(54) METHOD FOR TREATING THE LIQUID PHASE OF CONTAMINATED MATERIALS

(76) Inventor: Helmut Goeldner, Gewerbegebiet Oehmer Feld, D-31633 Leese (DE)

( * ) Notice: Subject to any disclaimer, the term of this patent is extended or adjusted under 35 U.S.C. 154(b) by 0 days.

(21) Appl. No.: 09/719,989

(22) PCT Filed: Jun. 16, 1999

(86) PCT No.: PCT/DE99/01774

§ 371 (c)(1),
(2), (4) Date: Dec. 19, 2000

(87) PCT Pub. No.: WO99/66963

PCT Pub. Date: Dec. 29, 1999

(30) Foreign Application Priority Data

Jun. 19, 1998 (DE) .......................................... 198 27 404

(51) Int. Cl.[7] .......................... A61L 11/00; A61L 2/00; A61L 9/00; C23F 11/00
(52) U.S. Cl. .............................. 422/1; 422/28; 422/29; 422/31; 422/106; 422/110; 422/292; 422/295; 422/299; 422/304; 422/305; 422/306; 422/307
(58) Field of Search ................................ 422/1, 26, 27, 422/28, 29, 31, 292, 295, 299, 304, 305, 306, 307, 106, 110

(56) References Cited

FOREIGN PATENT DOCUMENTS

EP          0-672-426 A1  *  1/1995

* cited by examiner

*Primary Examiner*—Robert J. Warden, Sr.
*Assistant Examiner*—Imad Soubra
(74) *Attorney, Agent, or Firm*—Crowell & Moring LLP

(57) ABSTRACT

A method for treating the liquid phase of contaminated materials that are disinfected or sterilized in a treatment chamber is provided, whereby a defined liquid collector area is provided in the treatment chamber. When the liquid in the collector area reaches a maximum level it is discharged into a collector tank and when the level of liquid in the collector area reaches a minimum level liquid is returned to the treatment chamber. When the liquid in the collector tank reaches a maximum level, liquid therefrom is returned to the treatment chamber in case the maximum level of liquid in the treatment chamber is not reached or said liquid is treated in an additional high-temperature disinfector unit to obtain purified liquid. A device that carries out the method is also provided. Using the method or device provided, contaminated solid materials with a high proportion of liquid can be disinfected or sterilized.

14 Claims, 2 Drawing Sheets

METHOD FOR TREATING THE LIQUID PHASE OF CONTAMINATED MATERIALS

The invention relates to a method for treating the liquid phase of contaminated materials, especially infected materials, which are fed in a treatment chamber to a high-temperature disinfecting apparatus, heated and disinfected or sterilized, and removed to a discharge, a defined collecting area for liquid being provided at the input end of the transport system in the treatment chamber.

The invention furthermore relates to an apparatus for treating contaminated materials, especially infected materials, in which the latter are delivered through an input unit to a transport system running in a treatment chamber, and heated and disinfected or sterilized, and are removed to a discharge, a defined area for collecting liquid being provided at the input end of the transport system in the treatment chamber.

In DE 197 17 839 a high-temperature disinfecting or sterilization apparatus has been described, which is suited especially for wastes specific to hospitals and in which the wastes are fed through in inlet hopper and a shredder to two screw conveyor sections arranged in tandem. The first screw conveyor is designed as a heating conveyor; it is inclined upward at an angle in its transport direction, thereby assuring that contaminated liquid which is introduced through the loading hopper will be able to collect only in the area below the loading hopper in a low-level screw conveyor section.

As long as a certain ratio of admixture of moist and dry wastes is kept within an average range, the liquid level in the lower part of the heated screw conveyor remains below the permitted maximum mark. If, however, large amounts of waste with a very high liquid content are introduced into the treatment apparatus, it can happen that the liquid level may rise above the permitted maximum mark in this area. This is because wastes in a purely liquid phase cannot, for obvious reasons, be conveyed by screw conveyors.

In U.S. Pat. No. 5,759,491 a method for treating infected materials is disclosed, in which the material to be treated is fed through a collecting area to a transport system which extends through the treatment chamber. There the heating as well as sterilization of disinfection takes place. The treated sludge is removed at the discharge end. Liquid can be pumped from a collecting tank into the collecting area or taken from the latter and pumped into the collecting tank.

EP-A-0 672 426 shows an apparatus for the treatment of infected wastes. Disinfection liquid is fed to the initially shredded wastes in a liquefaction station. This liquid is processed through a dewatering station adjoining a granulating and disinfecting station. The return of the disinfection liquid is thereby achieved.

Finally, DE 41 38 939 shows an apparatus and a method for the sterilization and disinfection of contaminated hospital waste. The granulated waste is thereafter fed to a disinfection screw conveyor and dried. Then follows a treatment with saturated steam and another drying.

The invention, therefore, is addressed to the problem of making available a method whereby even large amounts of purely liquid wastes produced in a short time can be safely treated independently of the treatment section actually designed for solid waste material in a high-temperature disinfecting apparatus. The invention is furthermore addressed to the problem in the treatment of contaminated materials, especially infected materials, which have a liquid phase and a solid phase, of providing an apparatus which will enable even large amounts of rapidly produced, purely liquid wastes to be safely disinfected or sterilized.

The problem is solved with regard to the method by a treatment of a kind in which when liquid which has collected in the defined collection area of the treatment chamber reaches a given maximum liquid level it is conveyed to a collecting tank, when the liquid level in the treatment reaches a given minimum level, liquid from the collecting tank is returned to the treatment chamber when the liquid level in the collecting tank reaches a given maximum, liquid is fed back from the collecting tank to the treatment chamber if the maximum liquid level has not been reached in the treatment chamber, and/or is treated in an additional high-temperature disinfecting unit for liquids only.

By discharging liquid from the defined collecting area of the treatment chamber to a collecting tank, it is brought about that the given maximum liquid level in the treatment chamber is not exceeded, and thus contaminated liquid cannot spread undesirably within the treatment chamber and endanger the treatment process. Since liquid is returned from the collecting tank to the treatment chamber in case liquid is needed in the latter, it is brought about on the other hand that sufficient moisture is always available in the treatment chamber for producing the necessary vapor pressure. To prevent a given maximum liquid level in the collecting tank from being exceeded, liquid from this tank is selectively either returned to the treatment chamber as long as the maximum liquid level has not been reached therein, or it is treated in an additional high-temperature disinfection unit for liquid only.

Thus, even when contaminated materials having a high liquid content are to be treated, reliable disinfection or sterilization of the solid content of the material is always assured, since contaminated liquid cannot propagate uncontrolled in the treatment chamber. Since the liquid content of the material is fed to an additional high-temperature disinfection unit or sterilization unit, the treated liquid waste can be delivered directly into a sewer line, for example.

Preferably, provision is made in the method so that liquid from the collecting tank is returned to the treatment chamber only when the liquid level in the treatment chamber has reached a preset minimum level. This means that, if the liquid level in the collecting tank has reached the preset maximum level, as a rule liquid from the collecting tank is treated in the additional high-temperature disinfection or sterilization unit for liquids only.

The high-temperature disinfecting unit can be comprised substantially of a heat exchanger in which the liquid to be treated is heated at least to a certain temperature and this temperature is maintained for as long as is necessary for disinfection or for a sterilization.

The disinfection or sterilization by means of the heat exchanger can take place continuously if a permanent excess pressure is produced in the heat exchanger such that the stream of treated liquid leaving the heat exchanger is reduced by a throttling means such that when delivered by a pump a pressure builds up in the heat exchanger.

If a heat exchanger is provided as an additional high-temperature disinfecting unit and liquid is returned from the collecting tank into the treatment chamber only when the liquid level in the treatment chamber falls to a given minimum—that is, when a maximum is reached liquid from the collecting tank is otherwise transported away through the heat exchanger—provision is made preferably such that the collecting tank will be emptied through the heat exchanger only down to a predetermined average liquid level. In this way it is assured that sufficient fluid will always remain in the collecting tank to enable the liquid level in the treatment chamber to be raised when the minimum level is reached, without the addition of fresh water.

Also, it can be arranged according to the invention that the liquid can be disinfected or sterilized in the collecting tank, that is, the additional high-temperature disinfecting unit is the collecting tank itself, and that in this case more untreated liquid can be collected in a buffer tank which is disposed between the treatment chamber and the collecting tank. In this case the heat exchanger connected at the end can be omitted.

It can be arranged that the defined collecting area for liquid in the treatment chamber is created by tilting the treatment chamber upward in the direction of feed. In this case liquid introduced into the treatment chamber collects in a lower area of the treatment chamber that is established by the inclination. Also, the transport system is based on one or more screw conveyors.

The task of the invention is achieved with regard to the apparatus by an apparatus of this type which additionally has the feature that the collecting area of the treatment chamber is connected by at least one liquid line to a liquid collecting tank such that liquid can be carried out of the collecting area of the treatment chamber into the collecting tank and from the collecting tank back to the treatment chamber.

In this way, it is achieved that the liquid level in the collecting area of the treatment chamber can be varied very flexibly. Thus, when a maximum level has been reached, liquid can be carried out of the treatment chamber into the liquid collecting tank in order to reduce the amount of liquid in the treatment chamber. On the other hand, if the liquid level reaches a minimum level in the treatment chamber, liquid also can be returned from the collecting tank to the treatment chamber in order to assure that there is sufficient liquid in the latter to produce the necessary vapor pressure.

Preferably, it is arranged for the liquid collecting tank to be connected by a line to carry liquid to a high-temperature disinfecting or sterilizing unit provided in addition to the treatment chamber. Thus, it is accomplished that liquid can be carried out of the liquid collecting tank to empty it at any time, and this liquid can be disinfected or sterilized in the treatment chamber independently of the actual treatment process. The liquid that is treated can be discharged directly into a sewer line.

This additional high-temperature disinfection or sterilization unit can be based on a heat exchanger.

Alternatively, the liquid collecting tank itself can be designed as the additional high-temperature disinfection unit or sterilization unit. In this embodiment of the apparatus, a buffer tank can be provided between the treatment chamber and the liquid collecting tank for additional untreated liquid coming from the treatment unit. Liquid can be returned as needed from this buffer tank to the treatment chamber.

Both the liquid collecting tank and the buffer tank can be vented or can operate on the principle of an air chamber. While in the first case a pump is needed to carry liquid from the collecting tank, in the case of a liquid collecting tank operating on the air chamber principle, an elevated pressure can be built up by feeding liquid into it, so as to drive the liquid out of it when an outlet on the liquid collecting tank is opened. Also, in the case of a liquid collecting tank operating on the air chamber principle, a possibility can be provided for pumping air into the tank in order to facilitate a complete emptying of the liquid collecting tank. The same applies correspondingly to the buffer tank.

Preferably, the treatment chamber is oriented upwardly so as to produce the defined collecting area for liquid in the treatment chamber. Also, it is preferable for the transport system to have one or more screw conveyors which extend into the treatment chamber.

The invention will be described below in further detail with respect to two working embodiments of the apparatus according to the invention, with reference being made to the drawing figures in which.

Figure 1:
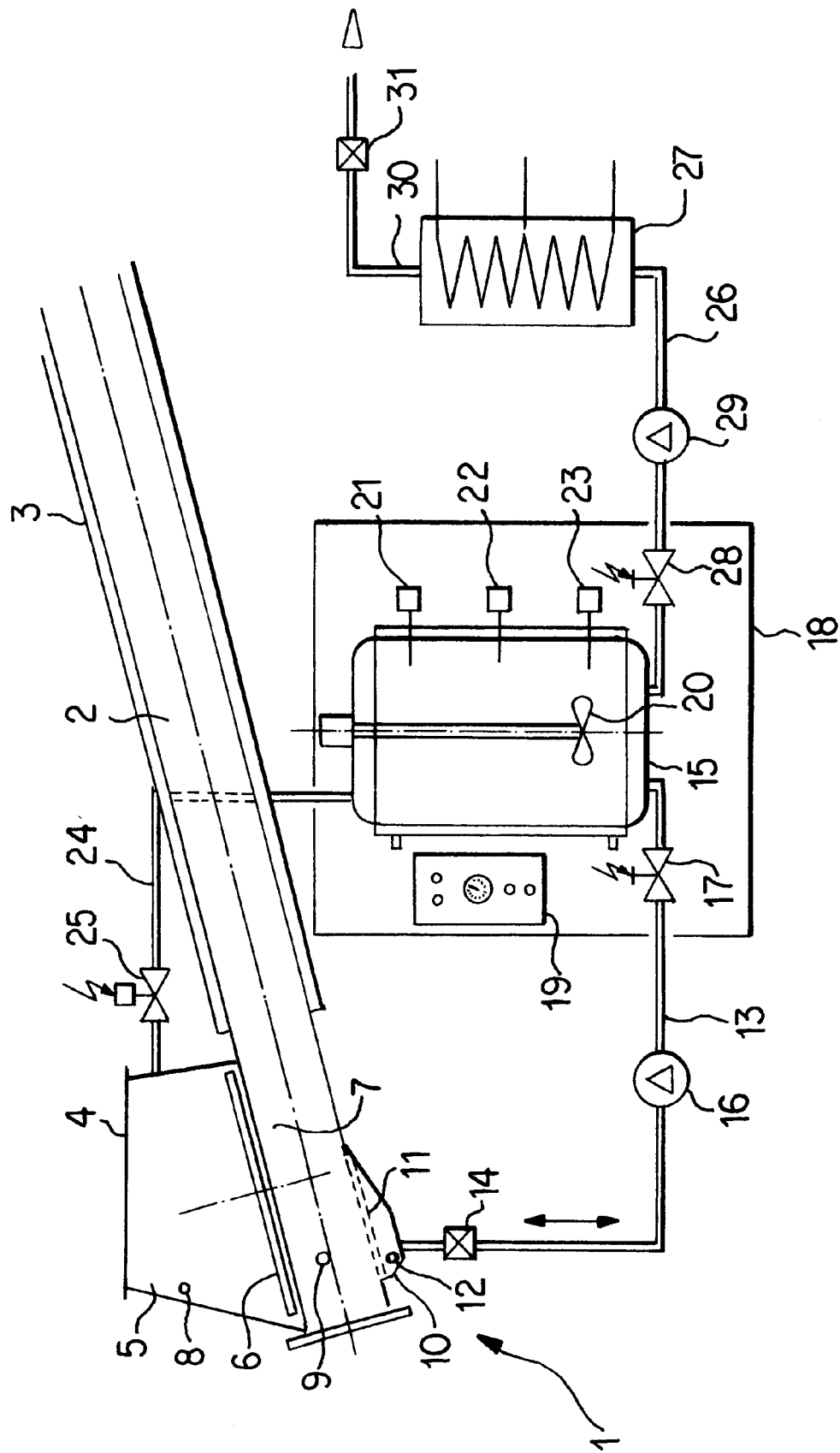
FIG. 1 shows a partial schematic representation of a first apparatus of the invention.

In the two figures, like parts are identified by the same reference numerals. The apparatus according to FIG. 1—identified by the reference number 1—has a treatment chamber 2 (shown only partially). A screw conveyor, not shown, extends over substantially the entire length of a first section of treatment chamber 2. The heating screw is provided over most of its length with a double jacket 3 in which a heat transfer oil is contained which is heated in a heating block, not shown.

The apparatus 1 furthermore has an feeder unit 4 with a bottom-dumping hopper 5 and a feed controller 6. Underneath the feeder unit 4, namely at the input end of the transport system provided by the heating screw, there is a defined collecting area 7 for liquid which is delivered together with contaminated solids into the bottom-dumping hopper 5. The defined collecting area 7 is created on the one hand by the established inclination of the treatment chamber 2, and on the other hand by a liquid indicator 8 which establishes a given maximum liquid level in the treatment chamber 2. Another liquid indicator 9, which is arranged within the treatment chamber 2, establishes a minimum liquid level in the treatment chamber 2.

A liquid outlet 10 of the treatment chamber 2 is situated underneath the liquid detector 9. The liquid outlet 10 is separated from the heating screw by the screen 11. An additional liquid level detector 12 is arranged within the liquid outlet 10 and gives a signal whenever there is no longer any liquid present in the treatment chamber.

A pipeline 13 is connected through a fitting 14 to the liquid outlet 10 and leads to a collecting tank 15 for liquid. Within the pipeline 13 is a positive displacement pump 16 and an electric ball valve 17.

The collecting tank 15 is arranged in a housing 18 which has a switch box 19. Also, the collecting tank 15 is equipped with a stirrer 20 and three liquid level detectors 21, 22 and 23. A venting line 24 with an electric valve 25 connects the bottom-dumping hopper 5 and the top end of the collecting tank 15.

An additional pipeline 26 leads from the bottom end of the collecting tank 15 to a heat exchanger 27. In pipeline 26 are once again an electric ball valve 28 and an unloading pump 29. At the outlet end the heat exchanger 27 is connected to another pipeline 30 which has a throttling and shut-off valve 31 and which extends, for example, to a conventional sewer line.

The apparatus 1 for the treatment of contaminated materials according to the invention is based on the following manner of operation.

Contaminated material is fed through the feeder unit 4 of the heating screw which extends inside of the first section of the treatment chamber 2. While the material being treated is conveyed by the heating screw, it is heated to a specific temperature. Furthermore, a compression of the material takes place in the heating screw such that a sealing plug of material is produced in its end area. At the end of the heating screw a second section (not shown) of the treatment chamber is provided in which an expansion and loosening up of the structure of the material takes place. In the second section of the treatment chamber a second screw conveyor is disposed to which the material is delivered by the heating screw. The second screw conveyor is in the form of a treatment screw for the material, and it is surrounded by a heating element. Energy can be delivered pulse-wise into the second section of the treatment chamber and into the treatment screw, and also steam can be supplied and/or generated and an elevated pressure and the temperature necessary for disinfection or sterilization is built up and maintained. The treatment screw compresses the material at its end to form a second sealing plug such that an elevated pressure can be maintained between the two material plugs acting as seals for a defined period of time. At the end of the treatment screw, there is a discharge for the treated material.

Due to the inclination of the heating screw, contaminated liquid, which is introduced into the feeder unit 4 together with solid materials, collects in the defined collecting area 7 of the treatment chamber 2. From this liquid reservoir, liquid also is transported, together with the solid material which is conveyed to the treatment screw by the heating screw, to the actual treatment screw and sterilized there.

It is arranged such that the liquid level in the collecting area 7 of the treatment chamber 2 will not drop below the minimum level established by the liquid detector 9. On the other hand, it must be assured that the liquid level will not exceed the maximum level established by the liquid detector 8.

When the liquid detector 8 indicates that the maximum level of liquid in the collecting area 7 has been reached, the ball valve 17 is opened and liquid is pumped by the positive displacement pump 16 from the collecting area 7 to the collecting tank 15. This continues until the liquid level in the collecting area 7 reaches the minimum level. Then the ball valve 17 is closed again. The collecting tank 15 is vented through the vent line.

If a need for additional liquid develops in the treatment chamber because the liquid level in the collecting area 7 falls below the minimum level, liquid is again pumped from the collecting tank 15 through the pipeline 13 into the collecting area 7 by means of the reversible positive displacement pump 16. This continues until either the maximum liquid level in the collecting area 7 is reached or until the liquid level in the collecting tank 15 has fallen to the level established by the level detector 23. This minimum fill level is necessary so that the stirrer 20 provided in the collecting tank 15 to prevent sedimentation will remain immersed in liquid.

If the liquid in the collecting tank 15 reaches the level defined by the additional liquid level detector 21 due to a greater amount of liquid produced in the treatment chamber, the ball valve 28 is opened and liquid is fed by the discharge pump 29 into the heat exchanger 27. This continues only until the fill level established by the level detector 22 is reached in the collecting tank 15. This assures that there will always be sufficient liquid present in the collecting tank 15 for return to the treatment chamber 2.

The sterilization process in heat exchanger 27 can be performed either continuously or discontinuously. In discontinuous operation the shut-off valve 31 at the end of heat exchanger 27 is closed, and the liquid placed under pressure by the discharge pump 29 remains in the heat exchanger 27 for the minimum residence time required for reliable sterilization. Then the shut-off valve 31 is opened, and the sterilized liquid is discharged from the heat exchanger 27.

In continuous operation the valve 31 is used as a throttle valve, with liquid being pumped continuously by the discharge pump 29 from the collecting tank 15 into the heat exchanger 27 and discharged through the throttle valve 31. This continuous operation is interrupted, of course, if the liquid level in the collecting tank 15 reaches the level established by the liquid level detector 22. In the case of continuous sterilization by the heat exchanger 27 the parameters are established so that every particle of liquid remains in the heat exchanger 27 for a sufficient length of time from its introduction into the heat exchanger 27 until its discharge through the flow regulating valve 31. Between the discharge pump 29 and the heat exchanger 27 a check valve (not shown) is provided so as to reliably prevent any backflow from the heat exchanger 27 to the collecting tank 15 when the discharge pump 29 is not running.

The heat exchanger 27 can be heated in a parallel flow by the same heat transfer oil which is provided for heating the treatment chamber 2 or heating screw conveyor.

As an alternative to the embodiment of the collecting tank 15 depicted in FIG. 1, a collecting tank can also be used which is based on the principle of the air chamber. In a collecting tank of this kind, the introduction of liquid causes pressure to build up within the collecting tank, which is utilized for discharging the liquid. In this case, air can be pumped through the vent line 24 whenever a fast and complete emptying of the collecting tank is to be performed. Alternatively, in such a case the air line 24 also could be omitted. If the collecting tank operates on the air chamber principle, another pressure source can additionally be provided connected to the collecting tank in order to create an additional possibility for producing an elevated pressure in the collecting tank.

Furthermore, unlike the apparatus shown in FIG. 1, it can also be arranged that the pipeline 13 is used only for conveying liquid to the collecting tank 15, and an additional pipeline is provided for returning liquid from the collecting tank 15 to the treatment chamber 2. In this case the pump 16 can be one that operates in only one direction, and valve 17 can be designed as a check valve.

Figure 2:
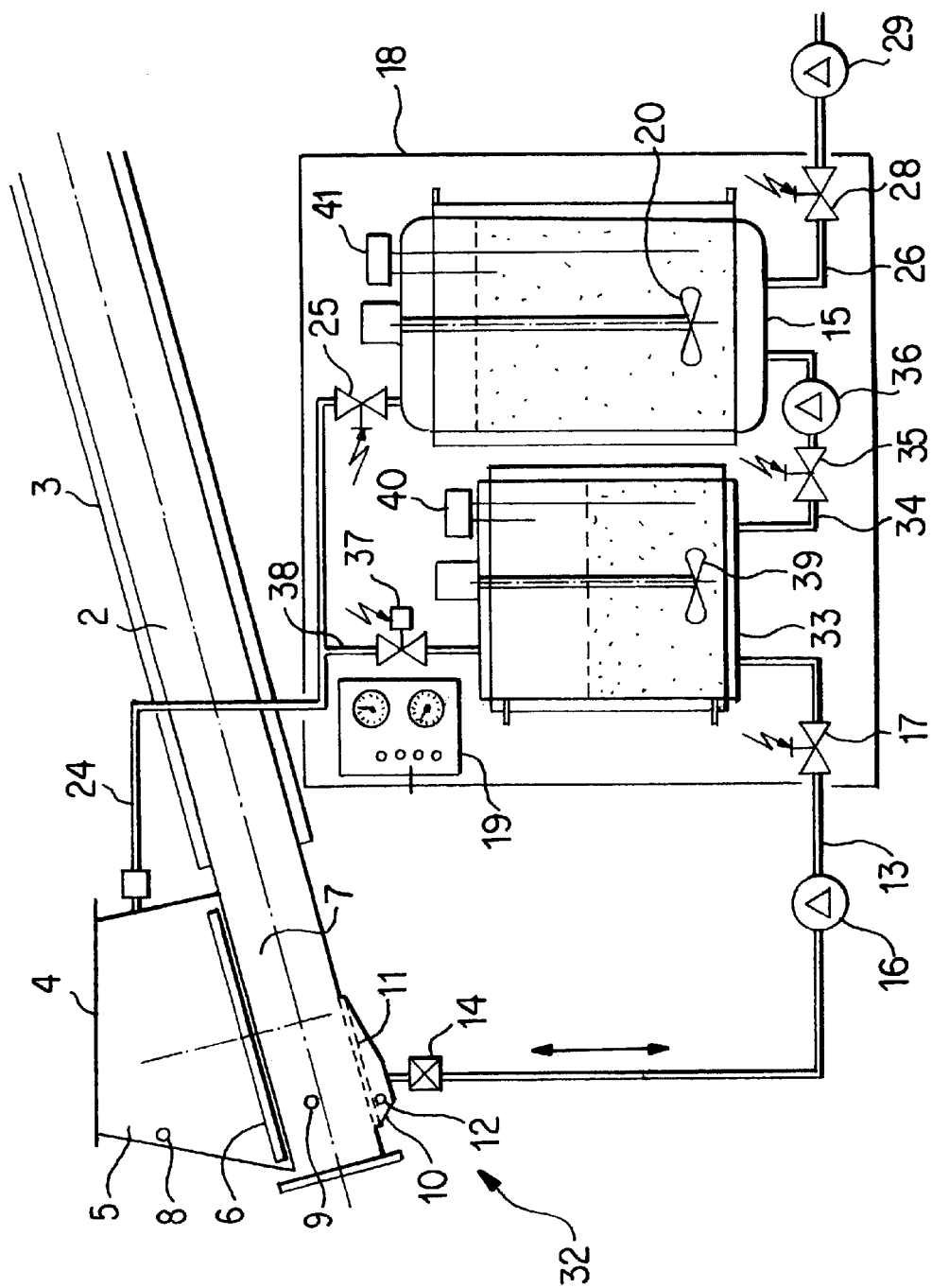
FIG. 2 shows a partial schematic representation of a second apparatus of the invention.

Reference will now be made to FIG. 2. In this figure an additional apparatus 32 according to the invention is shown. This apparatus differs from apparatus 1 shown in FIG. 1 substantially in that an additional tank 33 is provided which is arranged between the treatment chamber 2 and the collecting tank 15 and serves as a buffer tank. The buffer tank 33 and the collecting tank 15 are connected to one another by an additional pipeline 34. In this pipeline 34 an additional ball valve 35 and an additional positive displacement pump 36 are arranged.

The buffer tank 33 is connected to the vent line 24 by a vent line 38 provided with a valve 37.

The buffer tank 33 is connected via a vent line 38 having a valve 37 with the vent line 24.

The buffer tank 33 likewise has a stirrer 39. Both tanks 33 and 15 are provided with liquid level detectors 40 and 41, respectively, which each establish a minimum and a maximum liquid level in the tanks.

In the apparatus 32, the collecting tank 15 is designed so that in addition to the heat exchanger 27 shown in FIG. 1, the contaminated liquid can be autoclaved in it. During this sterilization process additional liquid being removed from the collecting area 7 of treatment chamber 2 can be collected in the buffer tank 33, and liquid can be returned from the buffer tank 33 to the treatment chamber 2.

In this apparatus 32 according to the invention, the liquid treated in the collecting tank 15 can be discharged directly into a sewer line. Another advantage of the apparatus 32 is that two tanks are present for collecting liquid from the treatment chamber 2, so that the individual tanks can be designed to be smaller.

Also in the case of apparatus 32, the two tanks 35 and 15 can be utilized which operate according to the air chamber principle.

What is claimed is:

1. A method for treating liquid portions of contaminated materials, comprising the steps of:

feeding the materials through a feeder unit to a transport system that extends through a treatment chamber of a disinfecting apparatus;

allowing liquid to collect in a defined area of the treatment chamber;

thermally disinfecting or sterilizing the materials while in the treatment chamber by heating the materials; and discharging the disinfected or sterilized materials at an outlet, wherein liquid collected in the defined area of the treatment chamber is discharged to a collecting tank upon reaching a first treatment chamber liquid level, liquid in the collecting tank is returned to the treatment chamber when liquid in the treatment chamber reaches a second treatment chamber liquid level, liquid in the collecting tank is returned to the treatment chamber when liquid in the collecting tank reaches a first collecting tank liquid level and when liquid in the treatment chamber is below first treatment chamber liquid level, and liquid in the collecting tank is transferred to a liquid only disinfecting unit when liquid in the collecting tank reaches a first collecting tank liquid level and when liquid in the treatment chamber is above a first treatment chamber liquid level.

2. Method according to claim 1, wherein the liquid from the collecting tank which is to be treated in the additional disinfecting unit for liquids only is passed through a heat exchanger in which it is heated to a temperature and held at the temperature for disinfection or sterilization.

3. Method according to claim 2, wherein the heating is performed continuously by means of a heat exchanger by producing a permanent elevated pressure in the heat exchanger by limiting the stream of treated fluid leaving the heat exchanger by means of a throttling device.

4. Method according to claim 2, wherein the liquid in the collecting tank is to be returned to the treatment chamber only if the liquid level in the treatment chamber reaches a given minimum, liquid is discharged from the collecting tank through the heat exchanger until the liquid level in the collecting tank has reached or fallen below the first collecting tank liquid level.

5. Method according to claim 1, wherein the liquid treated in the liquid only disinfecting unit is disinfected or sterilized in the collecting tank, and, additional untreated liquid is collected in a buffer tank which is arranged between the treatment chamber and the collecting tank.

6. Method according to claim 1, wherein the defined area of the treatment chamber is created by inclining the treatment chamber upwardly in the transport direction.

7. Method according to claim 1, wherein the transport system comprises a screw conveyor.

8. An apparatus to treat contaminated materials, comprising:

a transport system having a first end and a second end;

a feeder unit in communication with the first end of the transport system;

a first liquid detector located within the feeder unit;

a treatment chamber located within the transport system;

a first liquid line extending from the treatment chamber of the transport system to a liquid collecting tank and creating fluid communication between the treatment chamber and the liquid collecting tank;

a second liquid detector located within the liquid collecting tank;

a second liquid line extending from the liquid collecting tank to a liquid disinfecting unit and creating fluid communication between the liquid collecting tank and the liquid disinfecting unit;

a heating means provided around at least a portion of the transport system; and a discharge outlet at the second end of the treatment system.

9. Apparatus according to claim 8, wherein the liquid disinfecting unit comprises a heat exchanger.

10. Apparatus according to claim 9, wherein the liquid collecting tank is the liquid disinfecting unit.

11. Apparatus according to claim 10, further comprising a buffer tank between and in fluid communication with the treatment chamber and the liquid collecting tank, wherein the buffer tank is capable of receiving liquid from the treatment chamber.

12. Apparatus according to claim 8, wherein the liquid collecting tank operates in a manner of an air chamber.

13. Apparatus according to claim 8, wherein the treatment chamber is inclined upwardly in the transport direction.

14. Apparatus according to claim 8, wherein the transport system comprises a screw conveyor.

* * * * *